US005591216A

United States Patent [19]
Testerman et al.

[11] Patent Number: 5,591,216
[45] Date of Patent: Jan. 7, 1997

[54] METHOD FOR TREATMENT OF SLEEP APNEA BY ELECTRICAL STIMULATION

[75] Inventors: Roy L. Testerman, New Hope; Donald J. Erickson, Plymouth, both of Minn.

[73] Assignee: Medtronic, Inc., Minneapolis, Minn.

[21] Appl. No.: 446,191

[22] Filed: May 19, 1995

[51] Int. Cl.$^6$ .............................. A61B 5/08; A61N 1/372
[52] U.S. Cl. ............................ 607/42; 128/721; 128/725; 128/716
[58] Field of Search ............................. 607/42; 128/716, 128/721, 725

[56] References Cited

U.S. PATENT DOCUMENTS

| Re. 26,809 | 3/1970 | Hagfors | 128/418 |
|---|---|---|---|
| 3,405,715 | 10/1968 | Hagfors | 128/418 |
| 3,421,511 | 1/1969 | Schwartz et al. | 128/418 |
| 3,654,933 | 4/1972 | Hagfors | 607/118 |
| 3,955,560 | 5/1976 | Stein et al. | 128/640 |
| 4,341,221 | 7/1982 | Testerman | 128/642 |
| 4,570,631 | 2/1986 | Durkan | 128/204.23 |
| 4,573,481 | 3/1986 | Bullara | 128/784 |
| 4,602,624 | 7/1986 | Naples et al. | 128/784 |
| 4,777,962 | 10/1988 | Watson et al. | 128/716 |
| 4,830,008 | 5/1989 | Meer | 128/721 |
| 5,092,332 | 3/1992 | Lee et al. | 128/642 |
| 5,095,905 | 3/1992 | Klepinski | 128/642 |
| 5,123,425 | 6/1992 | Shannon, Jr. et al. | 128/848 |
| 5,143,067 | 9/1992 | Rise et al. | 128/642 |
| 5,174,287 | 12/1992 | Kallok et al. | 128/721 |
| 5,178,156 | 1/1993 | Takishima et al. | 128/724 |
| 5,190,053 | 3/1993 | Meer | 128/787 |
| 5,215,082 | 6/1993 | Kallok et al. | 607/42 |
| 5,265,608 | 11/1993 | Lee et al. | 128/642 |
| 5,344,438 | 9/1994 | Testerman et al. | 607/118 |
| 5,485,851 | 1/1996 | Erickson | 128/716 |

OTHER PUBLICATIONS

Remmers et al, "Pathogenesis of Upper Airway Occulsion During Sleep", *Journal of Applied Physiology*, 1978, vol. 44, pp. 931–938.

"Effects Of Electrical Stimulation Of The Genioglossus On Upper Airway Resistance In Anesthesized Dogs", Miki et al, *American Review Of Resp. Diseases*, (1989) vol. 140, pp. 1279–1284.

Miki et al, "Effects Of Submental Electrical Stimulation During Sleep On Upper Airway Patency In Patients With Obstructive Sleep Apnea", *American Review of Resp. Diseases*, 1989, vol. 140, pp. 1285–1289.

*Design and Evaluation of Nerve Stimulating Electrodes*, R. L. Testerman, Med. Res. Eng. 10: 6–11, 1971.

*A Nerve Cuff Technique for Selective Excitation of Peripheral Nerve Trunk Regions*, J. D. Sweeny, IEEE Trans. Biomed Eng. 37: 706–715, 1990.

*Selective Activation Using Peripheral Nerve Electrodes*, D. R. McNeil, Med. and Biol. Eng. & Comp., 23: 249–253, 1985.

*A Contribution to the Study of the Movements of the Tongue in Animals with Special Reference to the Cat*, Abd–el–Malek, J. Anat 73: 15–30, 1938.

*Selective Activation of Muscles Using Peripheral Nerve Electrodes*, D. R. McNeal, et al. Med. & Biol. Eng. & Comput., 1985, 23, 249–253.

*Gray's Anatomy*, Henry Gray, F. R. S., 1977, pp. 318–327 and 754–756.

Primary Examiner—William E. Kamm
Assistant Examiner—Carl H. Layno
Attorney, Agent, or Firm—Daniel W. Latham; Harold R. Patton

[57] ABSTRACT

A method for opening an upper airway of a patient by applying electrical stimulation to the patient's hypoglossal nerve includes positioning of an electrode into electrical contact with a selected portion of the patient's hypoglossal nerve, applying a stimulating electrical current from the electrode to the hypoglossal nerve and intraoperatively verifying the position of the electrode or adjusting the position of the electrode until it can be seen that the correct muscles of the upper airway are being stimulated. In particular, in an intraoperative setting it is possible to determine whether the correct muscles are being stimulated by looking for forward and contralateral extension of the patient's tongue or an increase in volume of the patient's oropharynx.

27 Claims, 5 Drawing Sheets

METHOD FOR TREATMENT OF SLEEP APNEA BY ELECTRICAL STIMULATION

BACKGROUND OF THE INVENTION

This invention relates to a method for treatment of obstructive sleep apnea and in particular to a method of treatment in which the hypoglossal nerve is stimulated in order to open the upper airway of a patient.

Sleep apnea has been known for some time as a medical syndrome in two generally recognized forms. The first is central sleep apnea, which is associated with the failure of the body to automatically generate the neuro-muscular stimulation necessary to initiate and control a respiratory cycle at the proper time. Work associated with employing electrical stimulation to treat this condition is discussed in Glenn, "Diaphragm Pacing: Present Status", Pace, V. I, pp 357–370 (July–September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to their collapse (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the dilator muscles. The dilator muscles are intimately linked to the respiratory muscles and these muscles respond in a similar manner to a stimulation or a depression of the respiratory center. The ventilatory fluctuations observed during sleep (alternately hyper and hypo ventilation of periodic respiration) thus favors an instability of the superior airways and the occurrence of oropharyngeal obstruction. The respiratory activation of the genioglossus has been particularly noted to be ineffective during sleep. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The electroencephalographic awakening which precedes the easing of obstruction of the upper airways is responsible for the fragmentation of sleep. The syndrome is therefore associated with an increased morbidity (the consequence of diurnal hypersomnolence and cardiovascular complications).

A method for treatment of obstructive sleep-apnea syndrome is to generate electrical signals to stimulate those nerves which activate the patient's upper airway muscles in order to maintain upper airway patency. For example, in U.S. Pat. No. 4,830,008 to Meer, inspiratory effort is monitored and electrical signals are directed to upper airway muscles in response to the monitored inspiratory effort. Or, in U.S. Pat. No. 5,123,425 a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. Or in U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of obstructive sleep apnea is assumed and electrical stimulation is applied to the musculature of the upper airway. Or, in U.S. Pat. No. 5,178,156 issued to Wataru et al, respiration sensing includes sensors for sensing breathing through left and right nostrils and through the mouth which identifies an apnea event and thereby triggers electrical stimulation of the genioglossus. Or, in U.S. Pat. No. 5,190,053 issued to Meer, an intra-oral, sublingual electrode is used for the electrical stimulation of the genioglossus to maintain the patency of an upper airway. Or in U.S. Pat. No. 5,215,082 issued to Kallok et at, upon sensing of the onset of an apnea event, a stimulation generator provides a signal for stimulating the muscles of the upper airway at a varying intensity such that the intensity is gradually increased during the course of the stimulation.

One problem which has not been addressed with these methods is that of how to ensure the stimulation of the correct muscular structures in the upper airway in each patient. For example, like many peripheral nerves, the hypoglossal nerve contains fascicles innervating antagonistic muscles like the genioglossus muscle which extends the tongue and alto the styloglossus muscle which retracts the tongue. In addition, the hypoglossal nerve is near other structures which should not be stimulated. Moreover, an electrode intended to stimulate the hypoglossal nerve must be placed through a minimal sized incision which makes anatomical identification difficult and, with the patient intubated, measurements of airflow are impossible. The effects of stimulating the hypoglossal nerve have been described in animal studies such as in Abd-El-Malek, *A contribution to the study of the movements of the tongue in animals, sith special reference to the cat*, J. Anat. 73:15– 30, 1938. Therefore, it is desirable to have a means for reliably stimulating only that portion of the nerve trunk which innervates the desired muscles or to have a means for selective placement of electrodes on specific portions of the hypoglossal nerve which are effective in opening the patient's airway.

It has been known for many years that a tripolar electrode arrangement can confine a stimulus current to the nerve cuff. (See e.g. Testerman, R. L. et al., *Design and evaluation of nerve stimulating electrodes*, Med Res Eng 10:6–11, 1971.) Also, as shown in Sweeny, J. D. et al., *A nerve cuff technique for selective excitation of peripheral nerve trunk regions*, IEEE Trans Biomed Eng 37:706–715, 1990, the tripolar arrangement of electrodes is more selective than a monopolar arrangement. This selectivity can be enhanced by the use of one or more "steering" electrodes. The electrode must be in dose contact with the nerve in order for the selectivity to work. (See e.g. McNeil, D. R. et al, *Selective activation using peripheral nerve electrodes*, Med & Biol Eng & Comput 23:249–253, 1985.) Several self-sizing cuff designs have been proposed which can fit snugly around the nerve without damage such as those disclosed in U.S. Pat. Nos. 4,573,481; 4,602,624; and 5,095,905. However, some of these designs tend to be fragile and difficult to install. An alternative to using these specialized electrodes is to use a more universal half-cuff design such as that disclosed in U.S. Pat. No. 5,344,438.

But, even if a half-cuff electrode is used, the surgeon implanting the electrode needs to be able to place the electrode precisely at the point on the nerve where effective stimulation can be applied to open the airway.

It is therefore an object of the present invention to provide a method for precisely locating one or more stimulation electrodes to selectively stimulate muscles to open the airway of a patient.

It is alto an object of the present invention to provide a method for selectively stimulating the nerve trunk of the hypoglossal nerve to selectively stimulate muscles to open the airway of a patient.

It is also an object of the present invention to provide apparatus for making a determination of correct electrode placement.

SUMMARY OF THE INVENTION

A method for opening an upper airway of a patient by applying electrical stimulation to the patient's hypoglossal nerve includes positioning of an electrode into electrical contact with a selected portion of the patient's hypoglossal nerve, applying a stimulating electrical current from the electrode to the hypoglossal nerve and then monitoring the patient's response to verify the position of the electrodes intraoperatively and/or to adjust the position of the electrode until it can be seen that the correct muscles of the upper airway are being stimulated. In particular, in an intraoperative setting it is possible to determine whether the correct muscles are being stimulated by looking for forward and contralateral extension of the patient's tongue or an increase in volume of the patient's oropharynx.

With this method, it has been found that specific locations on the hypoglossal nerve can be used to selectively stimulate the upper airway muscles so that airway patency is increased during the inspiratory phase of the respiratory cycle. For example, a portion of the hypoglossal nerve can be dissected from the fibers of the patient's genioglossus or hyoglossus muscle and stimulated to improve airway patency. Other candidates for improved airway patency is a location on a medial main nerve trunk or proximal main nerve trunk of the hypoglossal nerve. However, when stimulating some of these areas, it is necessary to avoid stimulation of all of the antagonistic muscles innervated by that nerve by using a multipolar electrode with the stimulation current applied to one or more selected electrode poles on the multipolar electrode so as to select the muscles to be stimulated. Preferably, at least the genioglossus muscle is stimulated and the hyoglossus and sternohyoid muscles are not activated in order to provide an improvement in the airway opening.

In a preferred method, the increase in volume of the oropharynx is identified by a decrease in pressure in a balloon occupying the patient's oropharynx. The stimulating electrical current is provided to the electrode in a series of regular pulses interrupted by intervals without a stimulating electrical current. When the balloon pressure decreases during the stimulation pulses, the stimulation is causing the volume of the oropharynx to increase which indicates that the stimulation is stimulating the correct muscles to improve airway patency by activating the dilator muscles.

The preferred method for testing the opening of the airway can be incorporated into an apparatus which will provide an instrumented indication of the correct positioning of the electrode. An electrode is positioned on the patient to be stimulated to stimulate the desired upper airway muscles, a pulse generator suitable for neurostimulation is connected to the electrode and a pressure transducer connected to a balloon or other device is used to identify an increase in volume of the patient's oropharynx in response to current supplied to the electrode. A series of stimulation pulses is sent to the electrode and the pulses are automatically transmitted to a recording device and/or a display device such as a strip recorder which marks the stimulation period. Also connected with the strip recorder is the output from the pressure transducer which provides a trace of the balloon pressure on the strip recorder. When the pressure in the balloon is shown to decrease as the stimulation is applied, an increase in volume of the oropharynx is indicated and the correct muscles are being stimulated to increase patency of the airway.

BRIEF DESCRIPTION OF THE DRAWINGS

FIG. 7 shows the reduction of pressure due to stimulation at a distal portion of the nerve. FIG. 8 shows the increase in pressure due to stimulation at a more proximal portion of the nerve.

DETAILED DESCRIPTION OF THE INVENTION

The present invention relates to a method for opening an upper airway of a patient by application of electrical stimulation which activates muscles of the patient's upper airway in a manner favorable to the patency of the airway.

Figure 1:
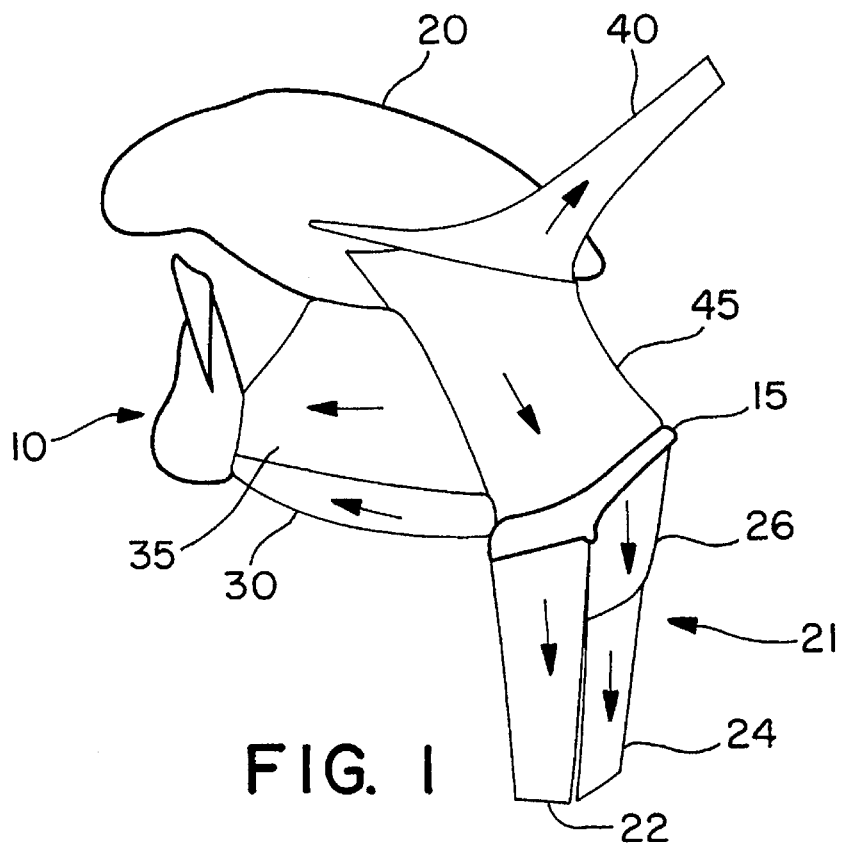
FIG. 1 is a schematic diagram showing the location and operation of the muscles of the upper airway.

Muscle structures of the upper airway are shown schematically in FIG. 1 together with the directional effects of their contractions on various airway structures. The symphysis and mental process portions of the lower jaw are indicated generally by numeral 10 while the hyoid bone is indicated by numeral 15. The tongue is indicated by numeral 20. Depressor muscles of the hyoid 15 and pharynx indicated generally by the numeral 21 include the sternohyoid 22, the sternothyroid 24 and the thyrohyoid 26. The sternohyoid 22 extends upward from the sternum and clavicle (not shown) and is attached to the hyoid 15. The sternothyroid 24 extends upward from the sternum and cartilage of the first rib (not shown) and is attached to the thyroid cartilage (not shown). The thyrohyoid 26 extends from the thyroid cartilage, appearing as an extension of the sternohyoid 24, and passes upward to attachment with the hyoid 15. These depressor muscles 21 depress the larynx and hyoid 15. Since a net forward force on the hyoid 15 and the tongue is desirable for increasing the opening of the upper airway, stimulation of the depressor muscles 21 should be avoided during stimulation of upper airway muscles. The geniohyoid muscle 30 is one of the elevator muscles of the hyoid 15. The geniohyoid muscle extends from the inner side of the symphysis of the lower jaw 10 to the hyoid 15. The geniohyoid muscle 30, as an elevator muscle for the hyoid 15 and the base of the tongue 20, will tend to increase the opening of the upper airway when stimulated to contraction. The genioglossus 35, styloglossus 40 and hyoglossus 45 muscles are extrinsic muscles of the tongue 20. The genioglossus 35 has points of attachment with the lower jaw 10, the tongue 20 and hyoid 15. The genioglossus 35, by means of its posterior fibers, draws the base of the tongue 20 forward so as to protrude the apex of the tongue 20 from the mouth. Contractile stimulation of the genioglossus 35 therefore also has the effect of increasing the opening of the upper airway. The styloglossus 40 extends from the styloid process (not shown) to the tongue. The styloglossus 40 therefore draws the tongue upward and backward. Contractile stimulation of the styloglossus 40 therefore tends to reduce the opening of the upper airway. The hyoglossus 45 extends from the hyoid 15 to the tongue 20. The hyoglossus 45 tends to retract the tongue 20 and to depress the tongue 20 at its sides so as to render it convex from side to side. Contractile stimulation of the hyoglossus 45 therefore tends to creates retraction and balling of the tongue 20 which is undesirable for increasing the opening of the upper airway.

Figure 2:
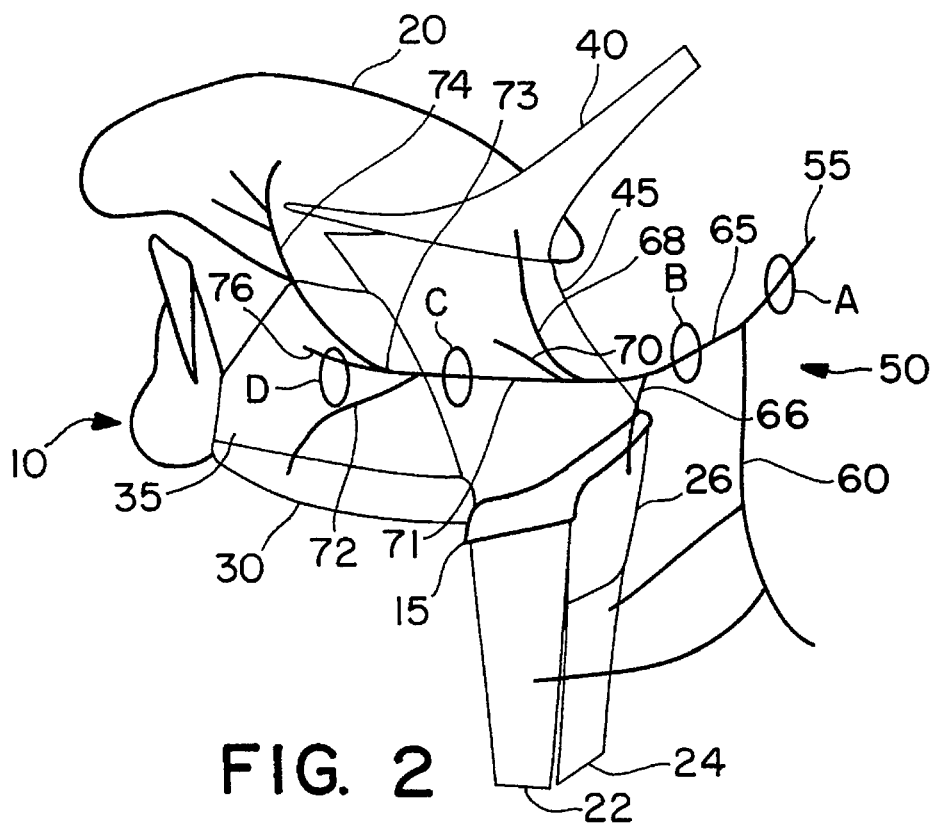
FIG. 2 is a schematic diagram showing the location of the hypoglossal nerve and its branches in relation to the muscles of the upper airway together with possible locations suitable for electrode placement.

The muscles indicated above are innervated by the hypoglosssal nerve as shown schematically in FIG. 2. The hypoglossal nerve indicated generally by numeral 50 includes a proximal main nerve trunk 55 which divides into the ansa cervicalis branch 60 and a first medial nerve trunk 65. The ansa cervicalis branch 60 innervates the sternothyroid muscle 24 and the sternohyoid muscle 22. The first medial nerve trunk 65 includes a branch 66 innervating the thyrohyoid muscle 26, a branch 68 innervating the styloglossus muscle 40, and a branch 70 innervating the hyoglossus muscle 45. An extension of the first medial nerve trunk 65 is a second medial nerve trunk 71 which has a branch 72 innervating the geniohyoid muscle 30. An extension of the second medial nerve trunk 71 is a third medial nerve trunk 73 which includes a branch 74 innervating the muscles of the tongue 20, and a branch 76 innervating the genioglossus muscle 35.

It can readily be appreciated that nonselective stimulation of the hypoglossal nerve 50 at the proximal main nerve trunk 55 would cause antagonistic contraction of muscles which would have an adverse effect on the opening of the upper airway. Therefore, stimulating nonselectively at reference point "A" of FIG. 2 causes all fibers in the hypoglossal nerve 50 to be activated. The net result is a net forward force on the hyoid 15 but the tongue 20 tends to pull back and down, restricting the airway. A similar restrictive result is also achieved by nonselective stimulation of the first medial nerve trunk 65 at reference point "B" of FIG. 2 except that depressor muscles 21 (i.e. the sternohyoid 22 and the sternothyroid 24) are not activated. Stimulation of the second medial nerve trunk 71 at reference point "C" of FIG. 2 further avoids activation of the thyrohyoid 26, the hyoglossus 45 and the sternoglossus 40 muscles. Therefore, the tongue 20 is pulled forward, increasing the opening of the upper airway. There is still some balling of the tongue 20 due to the mass action of the intrinsic tongue muscles. If the electrode were instead placed at reference point "D" on branch 76, the balling of the tongue would be alleviated. However, due to the practical difficulty of dissecting branch 76 from the underlying musculature to place the electrode, it may be necessary to accept some balling of the tongue by moving the electrode more proximally onto the third medial nerve trunk 73 or onto the second medial nerve trunk 71.

Therefore, with nonselective electrodes, clinically effective stimulation of the hypoglossal nerve 50 cannot be provided on the proximal main nerve trunk 55 or on the first medial nerve trunk 65. Selective stimulation of branch 76 of the hypoglossal nerve 50 at reference point "D" to innervate the genioglossus muscle 35 could be effective to improve airway patency if that could be operatively accomplished on the patient. Alternatively, selective stimulation of branches 74 and 76 by stimulation of the third medial nerve trunk 73 to innervate the genioglossus muscle 35 and the intrinsic muscles of the tongue 20 or branches 72, 74 and 76 by stimulation of the second medial nerve trunk 71 to innervate the genioglossus muscle 35, the geniohyoid muscle 30 and the intrinsic muscles of the tongue 20 could also be effective to improve airway patency. In yet another alternative, electrodes could be applied to both branches 72 and 76 to innervate the genioglossus muscle 35 and the geniohyoid muscle 30. With a selective, multipolar electrode, the electrode may be placed on the proximal main nerve trunk 55 at point "A" or on the first medial nerve trunk 65 with the optimal combination of electrode poles used to selectively stimulate the desired nerve fascicles. The effect is similar to placing whole nerve electrodes on the desired fascicles at a more distal point along the distal main nerve trunk 65.

In order to establish that an electrode (either a nonselective, whole nerve electrode or a selective, multi-polar electrode) is properly positioned in the patient is it desirable to intraoperatively evaluate the effect of a stimulation current provided to the electrode. The implantation procedure can be carded out generally as follows:

1. After introduction of general anesthesia, insert a nasal endotracheal tube for passage of gasses. This will allow unimpaired observation of tongue movement.

2. Prepare and drape the neck in the usual sterile fashion. Fully extend the neck, so that the lead can be implanted in its fully extended position.

3. Make a horizontal skin incision along a natural skin crease approximately 4 centimeters below the lower edge of the horizontal portion of the mandible. Extend the incision through the subcutaneous tissues and the platysmal muscle. Expose the digastric muscle.

4. Reflect the submandibular gland superiorly. Identify the hypoglossal nerve coursing in an anterior direction just above and medial to the anterior belly of the digastric muscle.

5. Follow the nerve distally until the nerve begins to branch, usually just beneath the posterior border of the mylohyoid muscle. Using blunt dissection, free enough of the hypoglossal nerve from the underlying hyoglossus muscle to allow the electrode to be inserted. Preferably, a half-cuff electrode is used such as that disclosed in U.S. Pat. No. 5,344,438, which is hereby incorporated by reference in its entirety. A whole nerve stimulating configuration of the electrode can be used in this location since the portion of the hypoglossal nerve exposed by this procedure is intended to correspond to a position approximating reference points "C" or "D" of FIG. 2.

Figure 4:
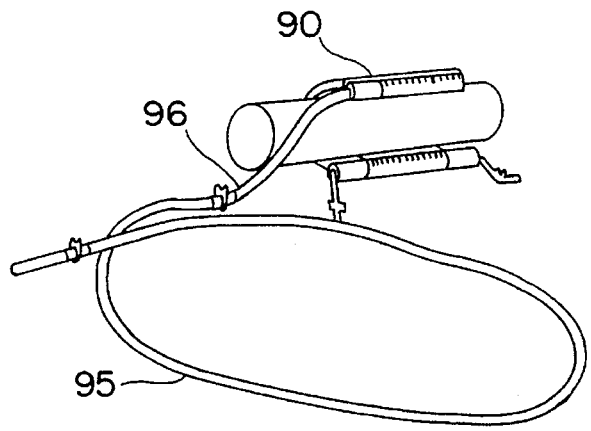
FIGS. 4 and 5 are perspective views of a half-cuff electrode and an associate lead in relation to a nerve. Two methods of appropriate strain relief technique for the lead are illustrated.
Figure 5:
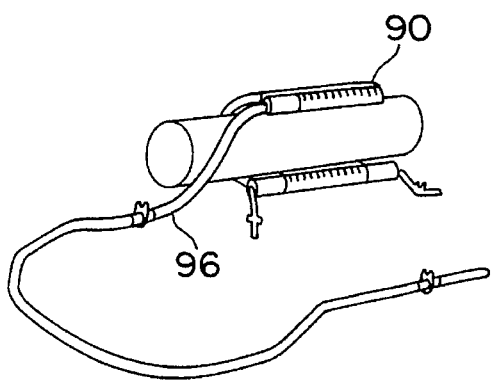

6. Just distal to the posterior of the mylohyoid muscle, the hypoglossal nerve generally splits into a medial and lateral bundle. As shown in FIGS. 4 and 5, place the electrode 90 on the medal bundle as shown in FIGS. 4 and 5. Since the anatomy is quite variable, the placement must be verified physiologically.

Figure 3:
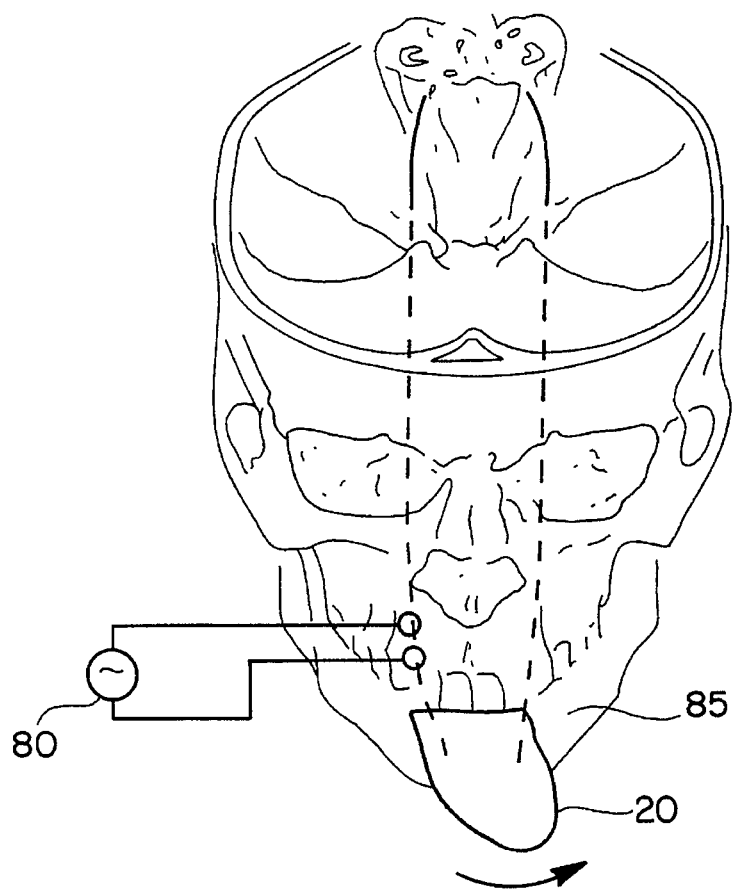
FIG. 3 is s schematic diagram of the head of a patient showing a forward and contralateral extension of the patient's tongue which is typical in response to effective stimulation.

7. Verify the effective placement by applying a stimulation current to the electrode. As shown in FIG. 3, with proper placement, the application of electrical current 80, the tongue 20 should extend forward and contralaterally with respect to the patient's mouth 85. With ineffective placement, the tongue is often pulled ipsilaterally. If placement is judged to be ineffective, the electrode should be removed and placed on a different branch of the hypoglossal nerve. The placement is then again verified by applying a stimulation current.

8. As shown in FIGS. 4 and 5, secure the electrode in place and secure the lead 96 in place with a strain relief loop 95 in the lead 96 extending from the electrode 90 near the electrode 90 or route the lead 96 so that strain will not be directly applied to the nerve.

Figure 6:
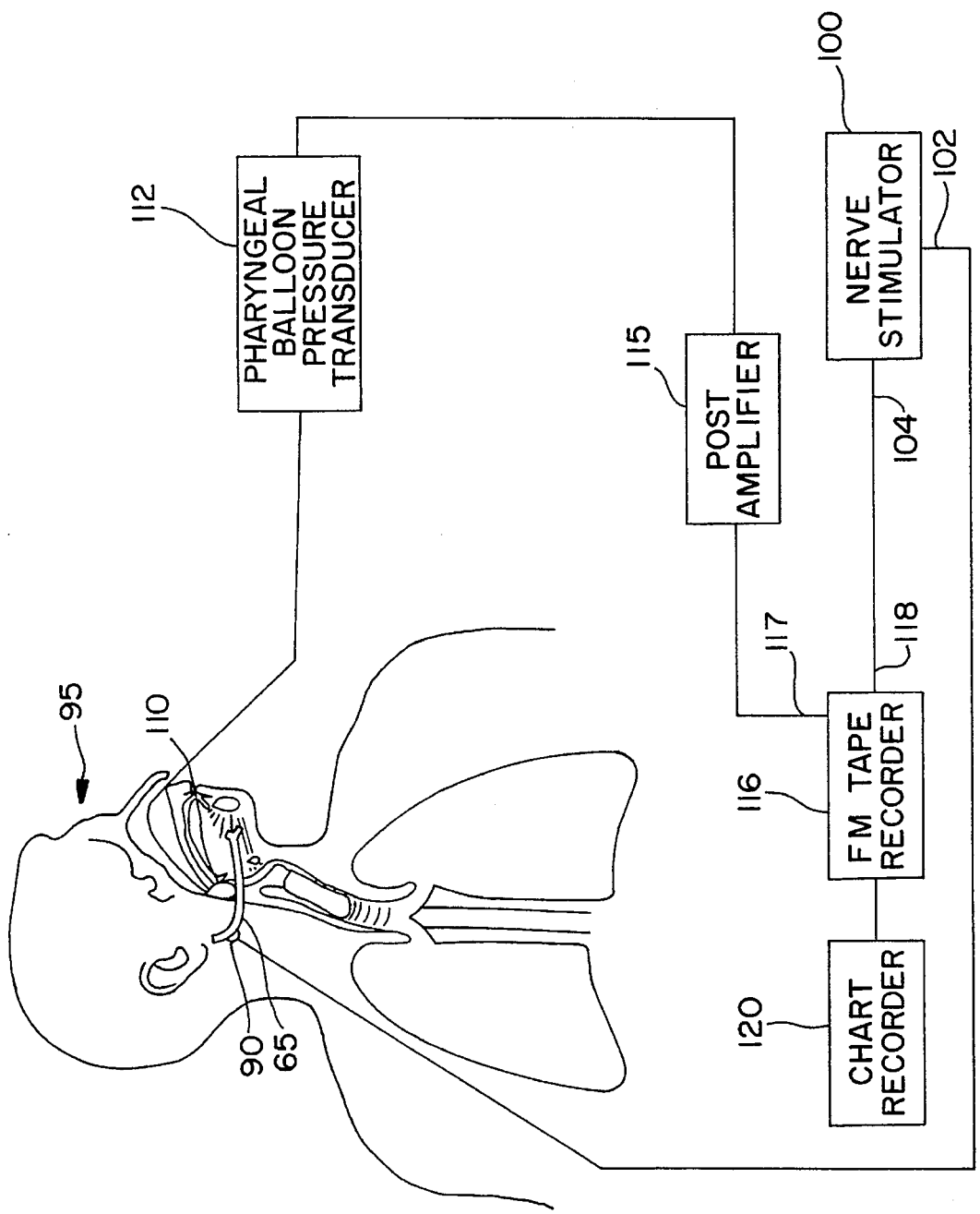
FIG. 6 is a schematic view of an apparatus for testing electrode positioning
Figure 7:
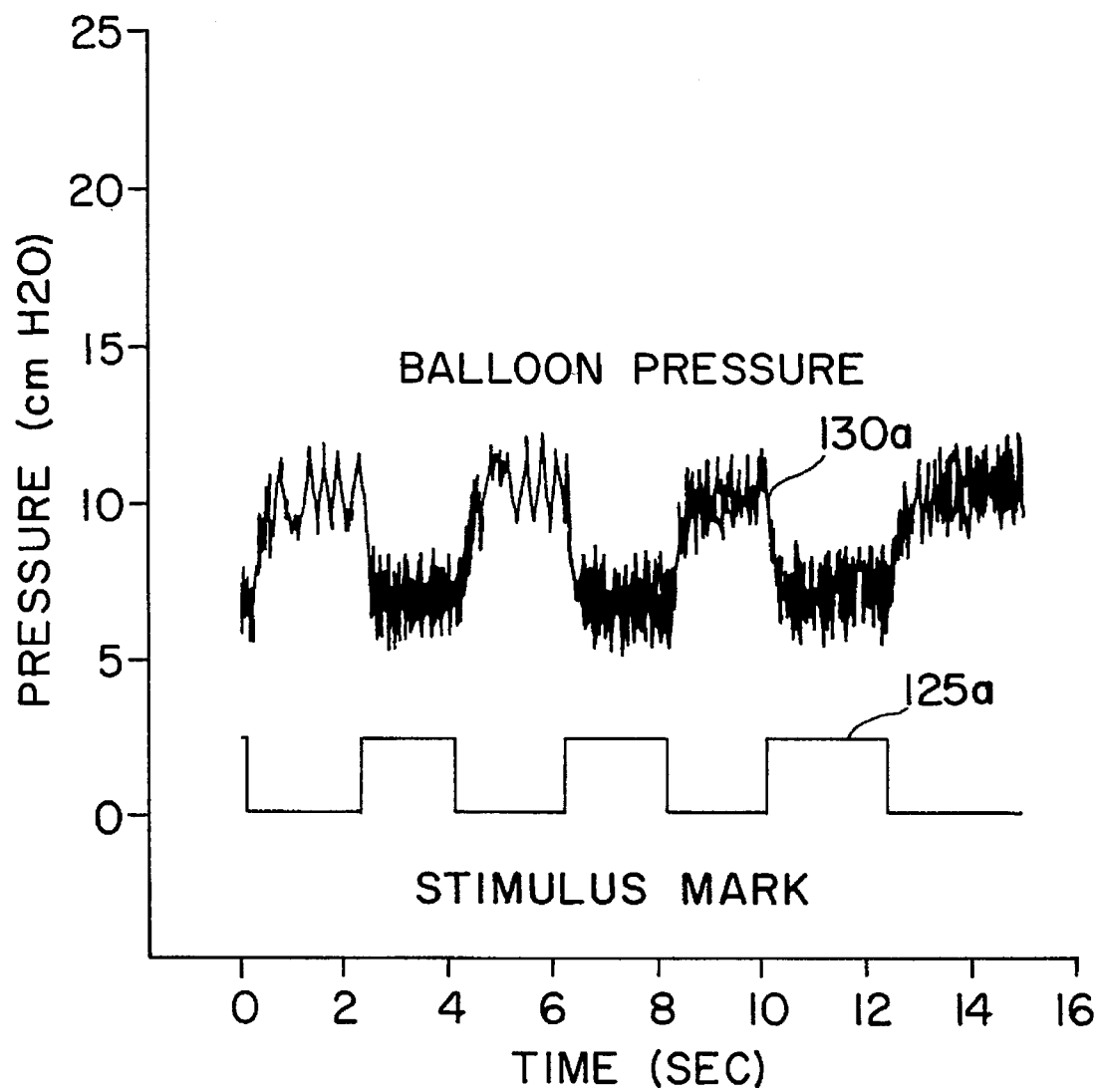
FIGS. 7 and 8 are charts showing traces of balloon pressure during stimulation and the effect of positioning an electrode in two different positions on the hypoglossal nerve.
Figure 8:
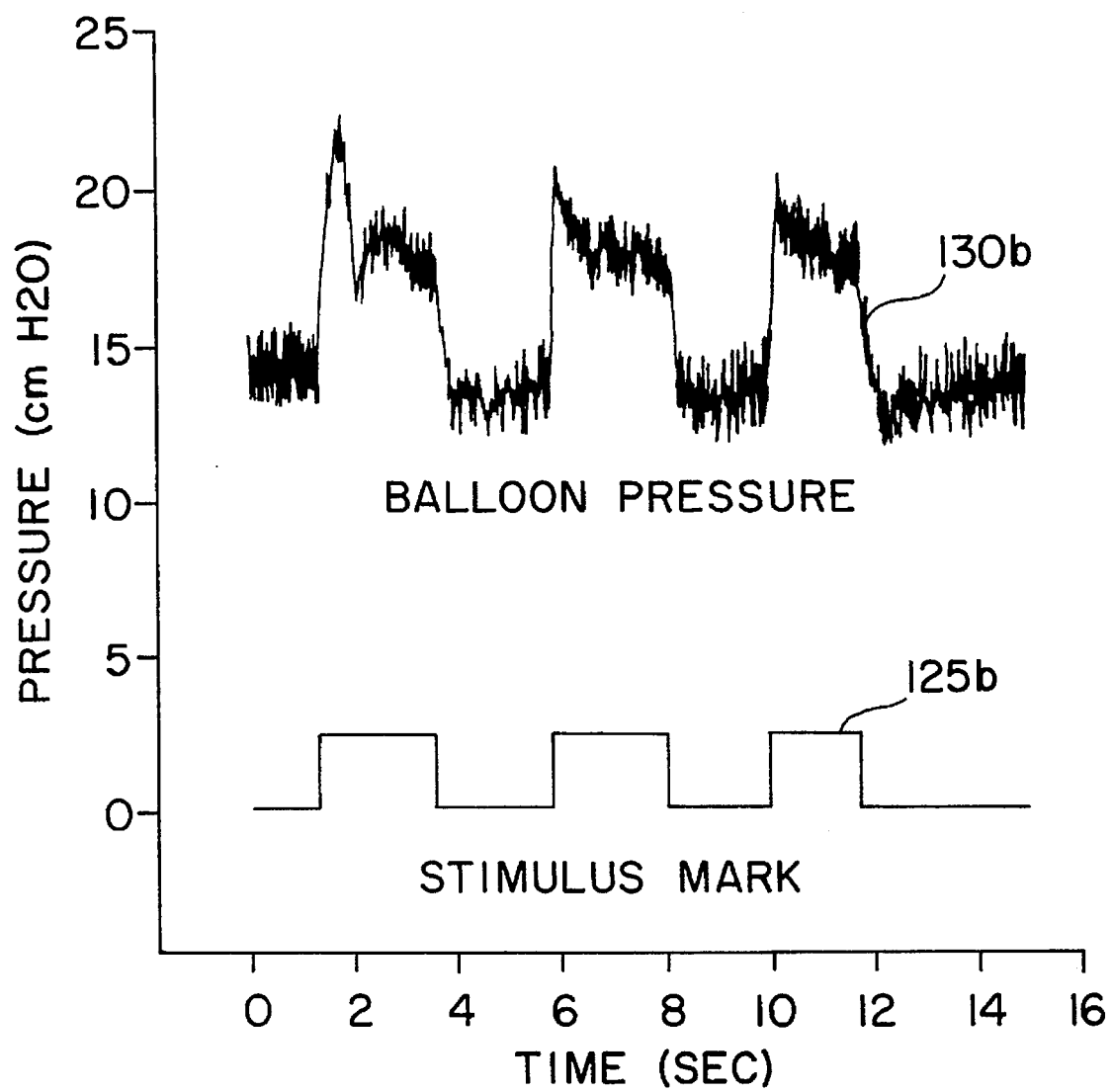

As an alternative to observing the tongue during the implantation procedure, a device for measuring the oropharynx can be used in order to determine whether the stimulation current applied to the electrode causes an increase in volume of the oropharynx showing the improvement in airway patency due to stimulation. For example, a balloon can be placed into the oropharynx with a measurement of balloon pressure used to identify the relative increase or decrease in volume of the oropharynx as stimulation is applied. FIG. 6 shows schematically an apparatus for carrying out such a pressure measurement. A patient 95 is shown with an electrode 90 on a portion of the distal main nerve trunk 65 of the hypoglossal nerve. The electrode 90 is connected to a nerve stimulator 100. The nerve stimulator 100 includes a stimulation output 102 for applying stimulation pulses to the electrode 90 and an monitoring output 104 for monitoring the stimulation signal. Conventional controls for amplitude, duration of stimulation and the like are also included. A balloon 110 is placed in the oropharynx of the patient 95 as shown. The balloon 110 is an elastic balloon that is inflated until it occupies the oropharynx. A Pressure transducer 112 monitors the pressure in the balloon and transmits a pressure signal to an amplifier 115 to an FM tape recorder 116 at a first input 117. The tape recorder 116 also includes a second input 118 to be connected to with the monitoring output 104 of the nerve stimulator 100. A chart recorder 120 is connected to the tape recorder 116 to monitor both a signal from the balloon 110 and from the nerve stimulator 100. The output from such an apparatus is shown in FIGS. 7 and 8. A first trace 125a, 125b indicates whether stimulation is turned on or off. The second trace 130a, 130b gives the pressure in the balloon as stimulation is turned on or off. Only the relative pressures are to be considered in the test since the absolute pressure depends on the original pressure to which the balloon 110 is inflated at the commencement of the test. The stimulating electrical current is provided to the electrode 90 in a series of regular pulses interrupted by intervals without a stimulating electrical current. As shown in FIGS. 7 and 8, a pulse duration and pulse interval of two seconds each is adequate to test the concept. If desired, the duration and frequency of the pulses can be made to simulate the pattern to be employed in the treatment of sleep apnea—e.g. with each pulse roughly as long as the inspiratory phase of the patient's respiratory cycle and with the interval between pulses roughly as long as the remainder of the respiratory cycle. As shown in FIG. 7, when the balloon pressure trace 130a decreases as the stimulation trace 125a indicates that the stimulation is turned on, the stimulation is causing the volume of the oropharynx to increase which indicates that the stimulation is stimulating the correct muscles to improve airway patency. This figure represents an electrode positioned at reference point "C" of FIG. 2. As shown in FIG. 8, when the wrong muscles are being stimulated the balloon pressure trace 130b shows an increase in balloon pressure as the stimulation trace 125b shows that stimulation is turned on. This indicates that the muscles being stimulated are actually constricting the airway and that the position of the electrode must be changed. This figure represents an electrode positioned at reference point "B" of FIG. 2.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. In a method for opening an upper airway of a patient by applying electrical stimulation to the patient's hypoglossal nerve, the improvement comprising:

(a) selecting a portion of the patient's hypoglossal nerve;

(b) positioning an electrode into electrical contact with the selected portion of the patient's hypoglossal nerve;

(c) applying a stimulating electrical current from the electrode to the hypoglossal nerve;

(d) monitoring the patient for a desired response, the desired response selected from the group consisting of:
   forward and contralateral extension of the patient's tongue; and
   an increase in volume of the patient's oropharynx;

(e) repeating steps (c) and (d) while adjusting the position for electrial stimulation on the nerve until the desired response is observed.

2. The method of claim 1 also comprising the step of dissecting the selected portion of the hypoglossal nerve from the fibers of the patient's genioglossus muscle, said step to be performed after the selecting step (a) and before positioning step (b).

3. The method of claim 1 also comprising the steps of inserting a balloon into the patient's oropharynx and determining the increase in volume of the oropharynx by a decrease in pressure in the balloon occupying the oropharynx.

4. The method of claim 1 wherein the stimulating electrical current is provided in a series of regular pulses interrupted by intervals without a stimulating electrical current.

5. In a method for opening an upper airway of a patient by applying electrical stimulation to the patient's hypoglossal nerve, the improvement comprising:

(a) selecting a portion of the patient's hypoglossal nerve;

(b) dissecting the selected portion of the hypoglossal nerve from the fibers of the patient's hyoglossus muscle;

(c) positioning an electrode into electrical contact with the selected portion of the patient's hypoglossal nerve;

(d) applying a stimulating electrical current from the electrode to the hypoglossal nerve; and (e) monitoring the patient for a desired response, the desired response selected from the group consisting of:
   forward and contralateral extension of the patient's tongue; and
   an increase in volume of the patient's oropharynx.

6. In a method for opening an upper airway of a patient by applying electrical stimulation to the patient's hypoglossal nerve, the improvement comprising:

(a) selecting a portion of the patient's hypoglossal nerve selected from the group consisting of a proximal main nerve trunk and a first medial nerve trunk;

(b) positioning a multipolar electrode into electrical contact with the selected portion of the patient's hypoglossal nerve;

(c) selecting at least one pole of the electrode for applied stimulation;

(d) applying a stimulating electrical current from at least one pole of the electrode to the hypoglossal nerve;

(e) monitoring the patient for a desired response, the desired response selected from the group consisting of:
    forward and contralateral extension of the patient's tongue; and
    an increase in volume of the patient's oropharynx (f) repeating steps (c) to (e) while adjusting the position of electrical stimulation on the nerve until the desired response is achieved.

7. In a method for opening an upper airway of a patient by applying electrical stimulation to the patient's hypoglossal nerve, the improvement comprising:

(a) selecting a portion of the patient's hypoglossal nerve selected from the group consisting of a second medial nerve trunk and a third medial nerve trunk;

(b) positioning an electrode into electrical contact with the selected portion of the patient's hypoglossal nerve;

(c) applying a stimulating electrical current from the electrode to the hypoglossal nerve; and (d) monitoring the patient for a desired response, the desired response selected from the group consisting of:
    forward and contralateral extension of the patient's tongue; and
    an increase in volume of the patient's oropharynx.

8. The method of claim 7 wherein the electrode is a multipolar electrode with the stimulation current applied to at least one selected electrode pole on the multipolar electrode.

9. In a method for opening an upper airway of a patient by applying electrical stimulation to the patient's hypoglossal nerve, the improvement comprising:

(a) dissecting a portion of the hypoglossal nerve from the patient's hyoglossus muscle;

(b) positioning an electrode into electrical contact with the dissected portion of the hypoglossal nerve;

(c) applying a stimulating electrical current from the electrode to the hypoglossal nerve; and (d) observing the patient for an indication of an opened airway.

10. The method of claim 9 wherein the indication of an opened airway is forward and contralateral extension of the patient's tongue.

11. The method of claim 9 wherein the indication of an opened airway is an increase in volume of the patient's oropharynx.

12. The method of claim 11 also comprising the steps of inserting a balloon into the patient's oropharynx and determining the increase in volume of the oropharynx by a decrease in pressure in the balloon occupying the oropharynx.

13. The method of claim 9 wherein the stimulating electrical current is provided in a series of regular pulses interrupted by intervals without a stimulating electrical current.

14. In a method for opening an upper airway of a patient by applying electrical stimulation to the patient's hypoglossal nerve, the improvement comprising:

(a) dissecting a portion of the hypoglossal nerve from the patient's genioglossus muscle;

(b) selecting a portion of the dissected nerve;

(c) positioning an electrode into electrical contact with the selected portion of the hypoglossal nerve;

(d) applying a stimulating electrical current from the electrode to the hypoglossal nerve; and (e) observing the patient for an indication of an opened airway;

(e) repeating steps (d) and (e) while adjusting the position of electrical stimulation on the nerve until the opened airway is observed.

15. The method of claim 14 wherein the indication of an opened airway is forward and contralateral extension of the patient's tongue.

16. The method of claim 14 wherein the indication of an opened airway is an increase in volume of the patient's oropharynx.

17. The method of claim 16 also comprising the steps of inserting a balloon into the patient's oropharynx and determining the increase in volume of the oropharynx by a decrease in pressure in the balloon occupying the oropharynx.

18. The method of claim 14 wherein the stimulating electrical current is provided in a series of regular pulses interrupted by intervals without a stimulating electrical current.

19. In a method for opening an upper airway of a patient by applying electrical stimulation to muscles of the patient's upper airway, the improvement comprising:

(a) selecting at least one muscle of the upper airway selected from the group consisting of the genioglossus muscle and the geniohyoid muscle;

(b) dissecting a selected portion of the hypoglossal nerve from the fibers of the patient's genioglossus muscle;

(c) positioning an electrode on the dissected nerve such that it may provide stimulation of the selected muscle;

(d) applying a stimulating electrical current through the electrode to stimulate the selected muscle;

(e) monitoring the patient for a desired response, the desired response selected from the group consisting of:
    forward and contralateral extension of the patient's tongue; and
    an increase in volume of the patient's oropharynx; and (f) repeating steps (d) and (e) while adjusting the position of electrical stimulation on the nerve until the desired response is observed.

20. The method of claim 19 wherein the stimulating electrical current is provided in a series of regular pulses interrupted by intervals without a stimulating electrical current.

21. In a method for opening an upper airway of a patient by applying electrical stimulation to muscles of the patient's upper airway, the improvement comprising:

(a) selecting at least one muscle of the upper airway selected from the group consisting of the genioglossus muscle and the geniohyoid muscle;

(b) selecting a portion of the hypoglossal nerve innervating the selected muscle;

(c) dissecting the selected portion of the hypoglossal nerve from the fibers of the patient's hyoglossus muscle;

(d) positioning an electrode on the dissected portion of the hypoglossal nerve such that it may provide stimulation of the selected muscle;

(e) applying a stimulating electrical current through the electrode to stimulate the selected muscle; and (f) monitoring the patient for a desired response, the desired response selected from the group consisting of:

forward and contralateral extension of the patient's tongue; and an increase in volume of the patient's oropharynx.

22. In a method for opening an upper airway of a patient by applying electrical stimulation to muscles of the patient's upper airway, the improvement comprising:

(a) selecting at least one muscle of the upper airway selected from the group consisting of the genioglossus muscle and the geniohyoid muscle;

(b) selecting a portion of the hypoglossal nerve innervating the selected muscle, the nerve portion selected from the group consisting of a proximal main nerve trunk and a first medial nerve trunk;

(c) positioning an electrode on the dissected nerve such that it may provide stimulation of the selected muscle;

(d) applying a stimulating electrical current through the electrode to stimulate the selected muscle;

(e) monitoring the patient for a desired response, the desired response selected from the group consisting of: forward and contralateral extension of the patient's tongue; and an increase in volume of the patient's oropharynx; and (f) repeating steps (d) and (e) while adjusting the position of electrical stimulation on the nerve until the desired response is observed.

23. In a method for opening an upper airway of a patient by applying electrical stimulation to muscles of the patient's upper airway, the improvement comprising:

(a) selecting at least one muscle of the upper airway selected from the group consisting of the genioglossus muscle and the geniohyoid muscle;

(b) selecting a portion of the hypoglossal nerve innervating the selected muscle, the portion of the hypoglossal nerve selected from the group consisting of a second medial nerve trunk and a third medial nerve trunk;

(c) positioning an electrode in the patient such that it may provide stimulation of the selected muscle;

(d) applying a stimulating electrical current through the electrode to stimulate the selected muscle; and (e) monitoring the patient for a desired response, the desired response selected from the group consisting of: forward and contralateral extension of the patient's tongue; and an increase in volume of the patient's oropharynx.

24. An apparatus for testing the opening of an upper airway of a patient when applying electrical stimulation comprising:

(a) electrode means positioned to provide stimulation to an upper airway muscle of the patient;

(b) electrical generating means for supplying current to the electrode; and (c) means for identifying an increase in volume of the patient's oropharynx in response to current supplied to the electrode including means for displaying an indication of the relative volume of the oropharynx as the stimulation is provided.

25. The apparatus of claim 24 wherein the electrode means comprises a nerve electrode positioned to stimulate a selected portion of the hypoglossal nerve.

26. The apparatus of claim 24 wherein the generating means includes means for providing a series of stimulation pulses interrupted by intervals without stimulation.

27. The apparatus of claim 24 wherein the means for identifying an increase in volume of the patient's oropharynx includes a balloon positioned in the patient's oropharynx.

* * * * *